United States Patent [19]
Piccoli et al.

[11] Patent Number: 6,118,037
[45] Date of Patent: Sep. 12, 2000

[54] PROCESS FOR THE REMOVAL OF CONTAMINANT COMPOUNDS CONTAINING ONE OR MORE HETEROATOMS OF SULFUR, NITROGEN AND/OR OXYGEN FROM HYDROCARBON STREAMS

[75] Inventors: Valerio Piccoli, Monza; Stefano Rossini, Milan; Domenico Sanfilippo, Paullo, all of Italy

[73] Assignee: Snamprogetti S.p.A., S. Donato Milanese, Italy

[21] Appl. No.: 09/056,628

[22] Filed: Apr. 8, 1998

[30] Foreign Application Priority Data

Apr. 22, 1997 [IT] Italy .................................. MI97A0936
Feb. 4, 1998 [IT] Italy .................................. MI98A0203

[51] Int. Cl.[7] ............................. C07C 7/12; C10C 25/00; B01J 20/34; B01J 20/02; B01J 20/10
[52] U.S. Cl. .......................... 585/820; 585/413; 585/448; 585/518; 585/824; 208/213; 208/245; 502/34; 502/55; 502/56; 502/405; 502/407
[58] Field of Search .................................. 502/34, 55, 56, 502/405, 407; 585/413, 448, 518, 820, 824; 208/213, 245

[56] References Cited

U.S. PATENT DOCUMENTS 5,187,131  2/1993  Tiggelbeck et al. ....................... 502/34
5,454,933  10/1995  Savage et al. ........................... 208/212

*Primary Examiner*—Walter D. Griffin
*Assistant Examiner*—Tam M. Nguyen
*Attorney, Agent, or Firm*—Oblon, Spivak, McClelland, Maier & Neustadt, P.C.

[57] ABSTRACT

Process for the removal of contaminant compounds containing one or more heteroatoms of sulfur, nitrogen and/or oxygen from hydrocarbon streams characterized in that it comprises:

an adsorption step in which said compounds are adsorbed by means of an adsorber essentially consisting of silica gel, possibly modified with one or more metals selected from the elements of groups IVb, Vb, VIb, VIII, Ib, IIb or from tin, lead or bismuth, carried out at a temperature of between 0° and 150° C. and at a pressure of between 1 and 20 atm;

an optional washing step with polar solvents or hydrocarbons;

and a regeneration step for removing the substances adsorbed by means of thermal treatment in a flow of inert gas carried out at a temperature of between 100° and 200° C.

8 Claims, No Drawings

PROCESS FOR THE REMOVAL OF CONTAMINANT COMPOUNDS CONTAINING ONE OR MORE HETEROATOMS OF SULFUR, NITROGEN AND/OR OXYGEN FROM HYDROCARBON STREAMS

The present invention relates to a process for the removal of contaminant compounds containing one or more heteroatoms of sulfur, nitrogen and/or oxygen, from hydrocarbon streams of varying composition and origin.

The presence of sulfurated, nitrogenated or oxygenated compounds is harmful in the treatment which these streams undergo, whether they be combustion or chemical conversion in refinery and/or petrochemical processes, preferably using heterogeneous catalysts. The combustion of compounds of sulfur and nitrogen present in fuels causes the formation of $SO_x$ and $NO_x$ which are harmful for the ecosystem and public health.

The presence of basic impurities, typically containing nitrogen, or oxygenated, even at an impurity level of less than one per cent, can considerably jeopardize the functioning of acid catalysts. The removal of heteroatoms such as nitrogen and sulfur is generally a very significant aspect in the treatment of crude oils and becomes even more necessary when heavy and/or poor quality cuts are used; less attention has been paid to the removal of impurities from light cuts such as $C_4$, $C_5$ streams from FCC units or from etherified streams in which, for example, oxygenated products are contained in small but potentially very harmful quantities downstream of subsequent processes (for example alkylation).

The removal of nitrogen and sulfur generally takes place by hydrogenating treatment under severe conditions of temperature and pressure, especially for cuts to be sent for hydrocracking and/or reforming. Patent literature is very ample: the removal of sulfur is generally carried out contemporaneously with the demetallation step: examples which can be cited are U.S. Pat. No. 4,746,419 of Amoco Corp., U.S. Pat. No. 4,652,361 of Phillips Petroleum Corp., U.S. Pat. No. 4,585,546 of Mobil where the elimination is carried out with catalysts based on inorganic oxides, for example alumina, modified with compounds/atoms with a hydrogenating function.

The methods for removing contaminants from light cuts can be divided into two categories:

a) chemical transformation of the functional group;

b) absorption on suitable material.

Disclosures are described hereunder, which can obtained from the art for some functional groups of interest.

The removal of nitrites which can damage acid catalysts for the synthesis of ethers or skeleton isomerization can be carried out as described in U.S. Pat. No. 5,414,183 which claims a basic hydrolysis in solution of NaOH at about 100° C. and under pressure (14–15 atm) in a static mixer.

Oxygenated products, alcohols or ethers can be contained in small quantities—at a ppm level—in etherification streams and even at such low levels can be harmful in downstream reactions which process these streams. For example ter-alkyl alcohols and MTBE can be contained in $C_5$ cuts from the production of TAME and must be removed to avoid the irregular consumption of the catalyst in alkylation. Other processes which are negatively affected by the presence of oxygenated products are polymerizations of olefins, for example isobutene with a high purity obtained from the cracking of MTBE, or processes carried out on zeolites owing to the great affinity. Methods for the removal of these oxygenated products are described in literature; for example teralkyl-alkyl ethers and the corresponding alcohols (MTBE, TAME, TBA, TAA) are decomposed by acid reaction catalyzed by materials based on silica at temperatures of 200°–250° C. as disclosed in EP-504980.

Sulfurated compounds (of the sulfuric and mercaptanic type) can be retained with an NaOH solution as in the Merox Process.

Type a) methods are specific however for the functional group and therefore when several contaminants having different functional groups must be removed it is necessary to subject the stream to more than one treatment. The type b) adsorption must be selective for contaminants with respect to the main components of the streams and also easy to regenerate. Disclosures in this sense are provided in U.S. Pat. No. 4,831,206 where the impurities containing sulfur and nitrogen are hydrogenated to hydrogen sulfide and ammonia in a first step and adsorbed in a second step by contact, which can take place in either liquid or solid phase (150°–290° C., 0.2–2 hours, 100–400 psig), with materials of the zeolitic type (4A, 5A and clinoptilotite). The adsorption beds are regenerated before being released by saturation.

An identical disclosure is provided in U.S. Pat. No. 4,831,207 as the differences are limited to the material (13X zeolite) and reactor configuration. Other zeolitic materials, such as X, Y, L, Beta zeolite and mordenite, are claimed in U.S. Pat. No. 5,120,881, the preferred being X in sodium form. The adsorption temperature can be deduced from the examples as being about 30°–35° C.

Recently the same applicant has claimed two processes using materials basically consisting of silica gel which combine a high adsorbing capacity (molecules retained per unit of mass of the adsorbing agent, under equilibrium conditions) for compounds containing heteroatoms of sulfur, nitrogen (IT-MI96A000772)and/or oxygen (IT-MI96000773) and a high adsorption rate of these molecules (molecules adsorbed per unit of time), at the same time allowing easy regeneration of this material.

The two processes comprise an adsorbtion step in which the contaminants are adsorbed by the adsorbing agent substantially consisting of silica gel carried out at atemperature ranging from 0° to 150° C. and a pressure ranging from 1 to 20 atms, and a regeneration step for removing the adsorbed substances by means of thermal treatment in a stream of inert gas, carried out at a temperature ranging from 100° to 200° C.

It has been found that for the two processes above described, instead of silica gel, a silica gel modified with one or more metals selected from elements of groups IVb, Vb, Vib, VIII, Ib, IIb or from tin, lead or bismuth can be used.

Besides, it has been observed however that for some types of charges (for example those also containing aldehydes, ketones or sulfurates) it is not possible to effect a complete regeneration, i.e. almost total removal of the contaminating compounds, with a consequant loss in the adsorbing capacity of the silica.

It has been also found that by carrying out a washing with a suitable solvent upstream of the regeneration, it is possible to obtain the complete regeneration of the silica gel, possibly modified, also for these types of charges.

The process of the present invention for selectively removing contaminant compounds from hydrocarbon streams, is characterized in that it comprises:

an adsorption step in which said contaminant compounds are adsorbed by means of an adsorber essentially consisting of silica gel, possibly modified with one or more metals selected from the elements of groups IVb, Vb, VIb, VIII, Ib, IIb or from tin, lead or bismuth, preferably selected from zinc, iron, molibden, vanadium, tungsten, tin, platinum, copper and chromium, carried out at a temperature of between 0° and 150° C. and at a pressure of between 1 and 20 atm;

a washing step, optional only in the case of silica gel modified, with polar solvents or hydrocarbons;

and a regeneration step for removing the substances adsorbed by means of thermal treatment in a flow of inert gas carried out at a temperature of between 100° and 200° C.

In the washing step, such as polar solvents, water, acetone, methanol, ethyl acetate or their mixtures, such as hydrocarbons, paraffins with from 5 to 8 carbon atom, or aromatic, can be used.

The washing step can be carried out in the same regeneration equipment.

The inert gas used in the thermal treatment can be elected from gases normally used for carrying out these regenerations, such as nitrogen, helium, steam, flue gas, air, etc.

The silica gel used can have a surface area preferably of more than 300 $m^2/g$, more preferably higher than 400 $m^2/g$, and a pore volume preferably of between 0.38 and 1.75 ml/g.

The possible modification of the silica gel consists in an addition, according to the known preparation techniques (preferably impregnation), of a quantity of the metals specified above so as to form a fraction of between 0.001 and 5% by weight with respect to the end catalyst.

The contaminants which are normally present in the hydrocarbon streams are:

among nitrogenated products: nitrites, such as acetonitrile or propionitrile, amines, such as alkylamines (propylamine, butylamine, ammonia, diethylamine, ethanolamine, etc.);

among sulfurated products: dialkylsulfides such as methylethylsulfide, mercaptans, such as n-butylmercaptan, alkylthiophenes, benzothiophenes, thiophene itself;

among oxygenated products: ethers, such as MTBE, alcohols, such as TBA, TAA, ketones and aldehydes, such as acetone, propionaldehyde, among diheteroatomic compounds, thiazoles, benzothiazoles, oxazoles, benzooxazoles, imidazoles, pyrazoles, etc, variously substituted and/or conjugated.

The streams taken under consideration can consist of hydrocarbons having between 3 and 8 carbon atoms, and are prevalently of a paraffinic, olefinic and possibly diolefinic nature or they can be complex mixtures, rich in aromatic hydrocarbons, characterized by an initial and final boiling point, as in the case of a fuel. They contain varying quantities of contaminants belonging to the above groups, approximately however of a thousand ppm.

In addition this material can contain various other components without these jeopardizing the specific performance described herein. A very interesting aspect of this material is that it has a moderate acidity under the applicative conditions, which is not sufficient to cause undesired polymerization or isomerization reactions in the hydrocarbon streams, mainly based on olefins, which are to be treated and which is not sufficient to react with the contaminant which would make it difficult to regenerate.

Another particular and surprising aspect of this material is that, if a stream is to be treated which contemporaneously contains paraffins and olefins, it does not preferentially adsorb the olefinic component, unlike adsorbing materials based on zeolites, such as 13X zeolite, which tends to preferentially retain the olefinic component thus altering the composition of the hydrocarbon stream which is being used.

Another aspect which is not less important than the others consists in the capacity of silica gel to selectively adsorb contaminants from hydrocarbon streams both in gas and liquid phase.

The removal of contaminants is generally a cyclic operation which comprises an adsorption phase and a regeneration phase of the material (desorption of the adsorbed contaminant). The times of each cycle phase are strictly related to the operating conditions in adsorption phase, such as for example the quantity of contaminant to be removed, the space velocity, pressure, operating temperature. It is easy to deduce that by increasing the loading of contaminant and space velocity the times of the adsorption phase are shortened, as the material is saturated more rapidly, or that on increasing the temperature the adsorbing capacity decreases.

The following examples, which should not be considered as limiting the invention, are provided to illustrate the experimental methods used in the examples relating to the application of silica gel in the removal of nitrogenated compounds (nitrites, amines) or sulfurated compounds (mercaptans, dialkylsulfides, thiophene).

EXAMPLES

Two types of experiments were carried out:

tests "in batch";

tests "in flow".

The adsorbing capacity (weight of contaminant/weight of adsorbing solid * 100) of various materials with respect to various contaminants were evaluated by means of in batch tests.

The in batch tests allowed the suitability of a given material to be used under flow conditions (which are more interesting for practical application) and also the maximum period of use for said material, to be determined.

The regenerability of the materials was verified by subjecting the exhausted material to thermal treatment in a flow of inert gas (air, nitrogen, etc.).

In short it was shown that modified silica gel has the capacity of selectively adsorbing contaminants (nitrogenated and sulfurated products) from hydrocarbon streams in both gas and liquid phase. It is also mechanically and chemically stable under the operating conditions and can be easily regenerated without losing its efficiency after repeated adsorption-regeneration cycles.

The tests "in batch" were carried out with a quantity of about 0.5–1 grams of adsorbing material which is put in contact with about 8–10 grams of mixture containing a certain quantity of one or more impurities in a closed pyrex container, at room temperature and a pressure equal to the vapour pressure of the mixture at the above temperature: the evolution of the composition of the liquid is analyzed by gas chromatography. The data obtained allow the quantity of contaminant which is adsorbed to be calculated.

The tests "in flow" were carried out as described below.

The adsorption bed consists of from 5 to 7 g of silica gel, previously dried at 150° C. and granulated at 25–60 mesh, charged into a tubular steel reactor with an internal diameter of 8 mm. The reactor is fed by means of a dosage pump for HPLC and is maintained at room temperature (22° C.) and at a pressure of 5 atm.

EXAMPLES 1–12

The preparation procedure of the materials of examples 1–12 is as follows:

The necessary quantity for obtaining the desired active phase loading, of a suitable salt, preferably nitrate, of the metal with which the silica gel is to be modified, is dissolved in a volume of water which is such as to impregnate with moderate wetting about 5–10 grams of carrier; the impregnation is carried out and the water is removed by gently heating the solid under movement.

The dried material is thermally treated at a temperature higher than the decomposition temperature of the counter-ion (generally about 300° C.) for a time of 2–4 hours. The material is granulated to 20–40 mesh and subjected to the test "in batch" described above.

The basic solution with which the tests were carried out consists of 60% by weight of n-hexane and 40% by weight of 1-pentene. For each test, a certain quantity of thiophene of about a thousand ppm by weight is added to an aliquot of this solution. The specific details and results are shown in Table I.

Active phase: referring to metal on final catalyst; Adsorbing capacity: (quantity of thiophene adsorbed [g]/weight of catalyst [g]) * 100 Thiophene removed: (quantity of thiophene adsorbed [g]/quantity of thiophene present in the solution) * 100.

EXAMPLE 13

The test was carried out according to the "in flow" procedure as described above.

5.01 grams of silica gel modified with Cr (% active phase:1) were charged. The preparation procedure of the material is analogous to that described in examples 1–12 except that the calcination temperature was 200° C. The solution fed has the following composition: 60% by weight of n-hexane, 40% by weight of 1-pentene and 1516 ppm of thiophene. The test conditions are: temperature 22° C., WHSV 1.89 $h^{-1}$, pressure 5 atm. The results are shown in Table II.

EXAMPLE 14

A material based on silica gel modified with 1 [%w] of copper is prepared according to the procedure described in example 13. A fuel cut characterized by Final Temperature of 225° C. and T90 of 190° C. containing 1280 ppm of sulfur, of which 60 of a mercaptan nature, and 50 ppm of nitrogen, of a prevalently benzothiazole type variously substituted, is fed onto this material (6.5 g) at room temperature and WHSV 2 $h^{-1}$. The treated cut has a content of 950 ppm of sulfur and a content of nitrogen of less than 2 ppm: therefore the percentage of contaminants removed is 25.9% for the sulfur whereas it is higher than 98% for the nitrogen. The mercaptanic sulfur was almost entirely removed (>95%). The characteristics of the fuel remained unaltered.

EXAMPLE 15

The material of example 14 is put in contact with a solution containing 1-pentene 40.1 [% w], n-hexane 59.25 [% w] and 6525 ppm of acetonitrile. The test is carried out at room temperature according to the "in batch" procedure with 0.35 g of solid and 9.2 g of solution. The adsorbing capacity of the material is 10.6% whereas the percentage of acetonitrile removed is 61.8.

EXAMPLE 16

The material of example 14 is put in -contact with a solution containing 1-pentene 40.1 [% w], n-hexane 59.25 [% w] and 6502 ppm of terbutyl alcohol. The test is carried out at room temperature according to the "in batch" procedure with 0.35 g of solid and 9.5 g of solution. The adsorbing capacity of the material is 12.2% whereas the percentage of terbutyl alcohol removed is 69.2.

EXAMPLE 17

A mixed $C_4$ charge of paraffins and olefins, containing 140 ppm of acetone, 10 ppm of acetonitrile and about 500 ppm of water (saturation water) is fed onto the material of example 14 (0.5 g). The test is carried out according to the "in flow" procedure at room temperature, at a pressure of 4 atm and WHSV of 20 $h^{-1}$. On continuously analyzing the outgoing stream the appearance of traces of acetone is observed after about 7 hours.

EXAMPLE 18

A liquid charge of $C_5$ hydrocarbons containing oxygenated products such as aldehydes and $C_3$ ketones, aldehydes and $C_4$ ketones and alcohols, mainly n-propanol, for a total of 0.71% by weight is subjected to the batch test described above, operating with 9.05 grams of charge and 1.03 grams of silica gel. The temperature is about 20° C.; the composition of the liquid phase is analyzed by GasChromatography after 30' from the beginning of test.

The material is subsequently subjected to removal treatment of the adsorbed product to re-establish the adsorbing capacity Q which can be obtained from the initial composition of the charge and from the composition of the hydrocarbon phase determined by GasChromatographic analysis.

The liquid is removed and the material is flushed with dry nitrogen at 20° C. to remove the liquid phase of extrapores. The solid is then put in contact with water in a ratio of about 4 gr. per gr. of solid for a time of approximately 10 minutes; this operation is repeated twice. When the last washing water has been removed, the temperature is gradually increased with dry nitrogen (40 scc/min) from 20° C. to 180° C. (v=57 cc/h).

Table III indicates the Adsorbing capacity variation ($\chi$) in relation to the regeneration treatments used.

The Adsorbing capacity Variation ($\chi$) is defined by the following formula:

$$\chi = (Q_n - Q_1)/Q_1 * 100$$

wherein $Q_n$=Quantity of impurities adsorbed in the nth cycle $Q_1$=Quantity of impurities adsorbed in the first cycle.

EXAMPLE 19—COMPARATIVE

The same liquid charge of hydrocarbons as example 1 is adsorbed by silica gel as described in example 1.

When the liquid phase has been removed, the material is flushed with dry nitrogen at 20° C. to remove the liquid phase of extrapores; it is then treated with nitrogen (40 scc/min), saturated with water at 20° C., and with a constant temperature increase to 190° C. in three hours (v=57 cc/h). The sample is maintained at this temperature for six hours. It is then cooled to 20° C. in a stream of dry nitrogen (anhydrous). The adsorption test described above is then repeated.

Table III indicates the Adsorbing Capacity Variation ($\chi$) in relation to the regeneration treatments used.

EXAMPLE 20

A material based on silica gel modified with 1% by weight of copper is prepared according to the following procedure.

The quantity necessary for obtaining the desired charge of active phase, of a suitable copper salt, preferably nitrate, is dissolved in a volume of water which is sufficient to impregnate with incipient wetting about 5–10 grams of carrier; the impregnation is effected and the water is removed by gently heating the solid under movement.

The dried material is thermally treated at a temperature higher than the decomposition temperature of the counter-ion (200° C.) for a time of 2–4 hours.

A fuel cut is fed onto this material (6.5 g) at room temperature and WHSV 2h-1, characterized by a Final Temperature of 225° C. and T90 of 190° C. containing 1280 ppm of sulfur, of which 60 of a mercaptane nature, and 50 ppm of nitrogen, of a prevalently benzothiazole nature variably substituted. The treated cut has a sulfur content of 950 ppm and a nitrogen content of less than 2 ppm; the percentage of contaminants removed is therefore 25.9% for the sulfur and more than 98% for the nitrogen. The mercaptane sulfur is almost completely removed (>95%). The characteristics of the fuel remain unaltered.

The material is subsequently subjected to removal treatment of the adsorbed product to re-establish the adsorbing capacity Q. The liquid is removed and the material is flushed with dry nitrogen at 20° C. to remove the liquid phase of extrapores. The solid is then put in contact with n-heptane in a ratio of about 4 gr. per gr. of solid for a time of approximately 10 minutes; this operation is repeated twice.

When the last washing n-heptane has been removed, the temperature is gradually increased with dry nitrogen (40 scc/min) from 20° C. to 180° C. (v=57 cc/h).

When the material has been brought back to room temperature, it is treated with the same charge under the same conditions; in this case the adsorbing capacity has undergone an overall variation (S+N) of +2.5%.

TABLE III

| | Adsorbing Capacity Variation (%) | |
|---|---|---|
| Cycle | Example 18 | Example 19-Comp. |
| 1 | 0 | 0 |
| 2 | 0.3 | −5.2 |
| 3 | 4.7 | −19.4 |
| 4 | −1.9 * | −29.5 |
| 5 | 2.2 | |
| 6 | −0.5 | |
| 7 | 1.3 | |
| 8 | 1.2 | |
| 9 | −1.7 § | |
| 10 | 3.1 | |

*: Regeneration carried out in a different way: the temperature increase, which was reached with the same rate, ended at 160° C., temperature at which the material was maintained for three hours.
§: Different washing solvent: acetone.

What is claimed is:

1. A process for removing contaminants containing sulfur, nitrogen and/or oxygen from a hydrocarbon stream, comprising:
    contacting a hydrocarbon stream with an adsorber consisting essentially of silica gel or silica gel modified with one or more elements selected from the group consisting of Group IVb, Vb, VIb, VIII, 1b, IIb, tin, lead and bismuth, said contacting step carried out at a temperature of between 0°–150° C. and a pressure of 1–20 atm;
    washing said adsorber with a polar solvent selected from the group consisting of water, acetone, methanol, ethyl acetate and mixtures thereof; and
    regenerating said adsorber by thermal treatment in a flow of inert gas carried out at a temperature of 100°–200° C.

2. The process according to claim 1 wherein the silica gel has a surface area of more than 300 m²/g.

3. The process according to claim 2 wherein the silica gel has a surface area of more than 400 m²/g.

TABLE I

| Ex. Nr. | 1 | 2 | 3 | 4 | 5 | 6 | 7 | 8 | 9 | 10 | 11 | 12 |
|---|---|---|---|---|---|---|---|---|---|---|---|---|
| Active phase | — | Zn | Fe | Fe | Mo | V | W | W | Sn | Sn | Pt | Pt |
| Active phase weight % | | 2.98 | 1.02 | 1.02 | 1.05 | 1 | 1 | 1 | 1 | 1 | 1 | 1 |
| Pretreatment | — | H2/300° | — | H2/300° | — | — | — | H2/300° | — | H2/300° | — | H2/300° |
| Adsorber (g) | 1.01 | 1.02 | 1.02 | 1 | 1.02 | 1.02 | 1.01 | 1.05 | 1.12 | 1 | 1.03 | 1 |
| Tio (ppm) | 1400 | 1448 | 1155 | 1527 | 1417 | 1515 | 1557 | 1459 | 1498 | 1406 | 1452 | 1518 |
| Adsorb. capaci | 0.231 | 0.254 | 0.176 | 0.290 | 0.244 | 0.29 | 0.282 | 0.226 | 0.268 | 0.243 | 0.168 | 0.191 |
| Tio removed | 19.9 | 22 | 17.7 | 23.4 | 21.2 | 23.4 | 22 | 19.5 | 23.3 | 20.3 | 14.1 | 15.2 |

TABLE II

| Time (min) | Fed cc | Tio out (ppm) | Adsorbed thiophene % |
|---|---|---|---|
| 15 | 3.6 | 17 | 99.4 |
| 45 | 10.8 | 474 | 89.0 |
| 75 | 18.2 | 1322 | 69.4 |
| 105 | 25.5 | 1460 | 51.9 |

4. The process according to claim 1 wherein the silica gel has a pore volume of between 0.38 and 1.75 ml/g.

5. The process according to claim 1 wherein the inert gas in the regeneration step is selected from nitrogen, helium, flue gas, air and steam.

6. The process according to claim 1 wherein the compounds are adsorbed in gaseous phase.

7. The process according to claim 1 wherein the compounds are adsorbed in liquid phase.

8. The process according to claim 1 wherein the metals are selected from zinc, iron, molybdenum, vanadium, tungsten, tin, platinum, copper and chromium.

* * * * *